Figure 1:
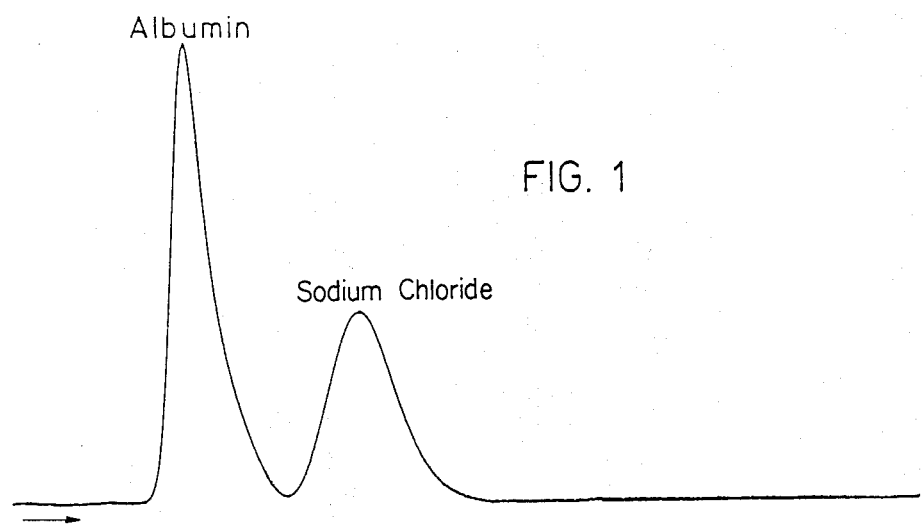

United States Patent [19]

Mitschker et al.

[11] Patent Number: 4,772,635

[45] Date of Patent: Sep. 20, 1988

[54] BEAD-SHAPED CROSSLINKED COPOLYMERS CONTAINING EPOXIDE GROUPS AND BASIC AMINO GROUPS, A PROCESS FOR THEIR PREPARATION AND THEIR USE

[75] Inventors: Alfred Mitschker, Odenthal; Peter M. Lange, Leverkusen, both of Fed. Rep. of Germany; Wolfgang Kreiss, New Martinsville, W. Va.

[73] Assignee: Bayer Aktiengesellschaft, Leverkusen, Fed. Rep. of Germany

[21] Appl. No.: 934,877

[22] Filed: Nov. 25, 1986

[30] Foreign Application Priority Data

Dec. 7, 1985 [DE] Fed. Rep. of Germany ....... 3543348

[51] Int. Cl.$^4$ .......................... C08D 5/20; C08F 24/00; C08C 19/22
[52] U.S. Cl. ....................................... 521/34; 526/273; 526/261; 525/379; 525/381; 525/382; 525/380
[58] Field of Search ................... 521/34; 525/379, 380, 525/381, 382; 526/273, 261

[56] References Cited

U.S. PATENT DOCUMENTS

| | | | |
|---|---|---|---|
| 2,630,427 | 3/1953 | Hwa | 521/34 |
| 2,630,429 | 3/1953 | Hwa | 521/34 |
| 4,205,148 | 5/1980 | Tatsukomi et al. | 525/379 |
| 4,224,415 | 9/1980 | Meitzner et al. | 521/38 |

Primary Examiner—Joseph L. Schofer
Assistant Examiner—Peter F. Kulkosky
Attorney, Agent, or Firm—Sprung Horn Kramer & Woods

[57] ABSTRACT

The invention relates to new bead-shaped crosslinked macroporous copolymers containing epoxide groups and basic amino groups, which are obtainable by reacting polymerizable glycidyl compounds, before or during free radical bead polymerization, which is carried out in the presence of agents which impart porosity and, if appropriate, with the addition of polyvinyl compounds which can be polymerized by free radical polymerization, with amines which are capable of reacting with at least two epoxide groups, a process for their preparation and their use, for example, for binding biologically active substances, for the preparation of strongly basic anion exchangers and hydrophilic chromatography resins for biomaterials.

13 Claims, 1 Drawing Sheet

BEAD-SHAPED CROSSLINKED COPOLYMERS CONTAINING EPOXIDE GROUPS AND BASIC AMINO GROUPS, A PROCESS FOR THEIR PREPARATION AND THEIR USE

The invention relates to new macroporous bead-shaped crosslinked copolymers containing epoxide groups and basic amino groups, a process for their preparation and their use.

Bead polymers of crosslinked copolymers containing epoxide groups are known. Thus, for example, various hydrophilic, crosslinked copolymers which contain epoxide groups and are prepared by inverse bead polymerization are described in DE-AS (German Published Specification) No. 2,237,316 (=U.S. Pat. No. 4,070,348), DE-OS (German Published Specification) No. 2,343,633 (=U.S. Pat. No. 4,070,348) and No. 2,722,751 (=U.S. Pat. No. 4,190,713) and European patent No. B1-0,058,767 (=U.S. Pat. No. 4,511,694).

These copolymers are built up from monomers which have a binding activity towards proteins, for example glycidyl (meth)acrylates or glycidyl vinyl or allyl ethers, crosslinking monomers, such as glycol di-(meth)acrylate and/or methylene-bis-(meth)-acrylamide, and hydrophilic monomers, for example monomers containing hydroxyl groups. According to DE-OS (German Published Specification) No. 2,722,751, the formation of hollow beads is achieved by using certain amounts of crosslinking monomers and (meth)acrylamides. According to European patent No. B1-0,058,767, copolymers with a particularly high bonding capacity for certain enzymes are obtained by using certain diluent mixtures during the inverse bead polymerization.

Gelatinous, macroporous bead polymers of crosslinked copolymers, containing epoxide groups, of glycidyl monovinyl esters or glycidyl monovinyl ethers and alkylene glycol divinyl esters are known from German patent Spec. No. 2,728,146 (=U.S. Pat. No. 4,118,347). These copolymers are prepared by free radical aqueous suspension polymerization of the monomers in the presence of organic diluents which dissolve the monomers, and are converted into modified copolymers which are free from epoxide groups by hydrolysis or alcoholysis of the epoxide groups.

Macroporous bead polymers of crosslinked copolymers, containing epoxide groups, of glycidyl methacrylate and ethylene dimethacrylate are described in Angew. Makromol. Chemie 117 (1983) 117–129. They are prepared by customary bead polymerization in aqueous suspension in the presence of various agents which impart porosity.

It has now been found that new macroporous, crosslinked copolymers which contain epoxide groups, have favourable binding properties for biologically active substances and have diverse uses are obtained by customary bead polymerization in aqueous suspension if polymerizable glycidyl compounds, such as glycidyl (meth)acrylates and glycidyl vinyl and/or glycidyl allyl ethers are reacted, before or during the free radical bead polymerization, which is carried out in the presence of agents which impart porosity and, if appropriate, also using polyvinyl compounds which can be polymerized under free radical conditions, with amines which are capable of reacting with at least two epoxide groups, the epoxide ring being opened. By using the amines which are capable of reacting with at least two epoxide groups, bead-shaped copolymers which have more advantageous binding properties for biologically active substances and have more diverse uses than the already known bead-shaped copolymers based on polymerizable glycidyl compounds which, apart from epoxide groups, contain only hydroxyl groups are obtained. The amines serve simultaneously as the crosslinking agents and as basic modifiers for the polymerizable glycidyl compounds. The amines also effect the development of particular pore structures in the copolymer.

The invention thus relates to new bead-shaped macroporous crosslinked copolymers containing epoxide groups and basic amino groups, which are obtainable by a process in which polymerizable glycidyl compounds, preferably glycidyl (meth)acrylates, glycidyl vinyl ethers and/or glycidyl allyl ethers, are reacted, before or during the free radical bead polymerization, which is carried out in the presence of agents which impart porosity and, if appropriate, with the addition of polyvinyl compounds which can be polymerized under free radical conditions, with amines which are capable of reacting with at least two epoxide groups.

The invention furthermore relates to a process for the preparation of these new macroporous, bead-shaped crosslinked copolymers containing epoxide groups and basic amino groups; the process is characterized in that polymerizable glycidyl compounds are subjected to bead polymerization in a manner which is known per se, if appropriate with the addition of polyvinyl compounds which can be polymerized under free radical conditions, in aqueous suspension in the presence of agents which impart porosity and agents which form free radicals, and the polymerizable glycidyl compounds are reacted, before or during the polymerization, with amines which are capable of reacting with at least two epoxide groups.

Figure 2:
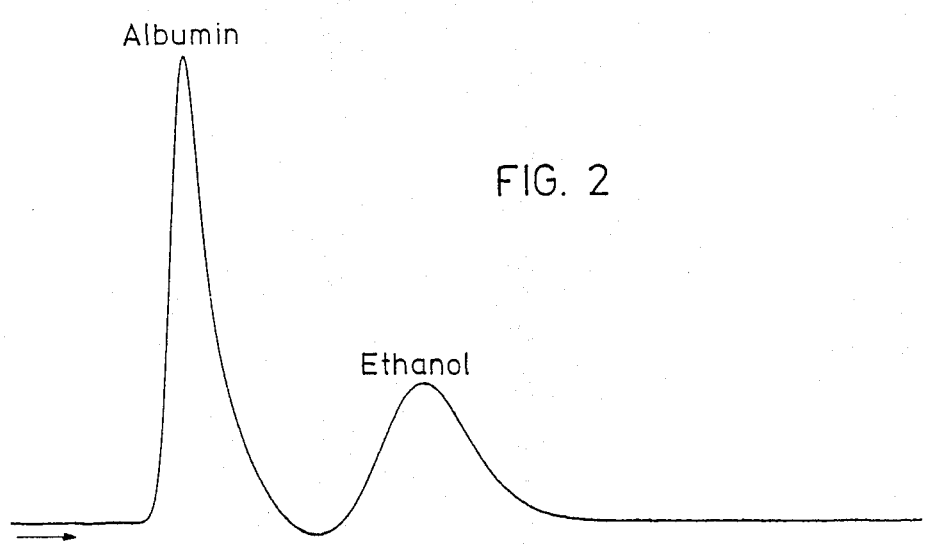

FIG. 1 and FIG. 2 are plots which demonstrate the effectiveness of the claimed bead polymers of the invention when used as adsorbents for chromatographic separations.

FIG. 1 concerns the desalination of (separation of NaCl from) a protein solution using an inventive polymer.

FIG. 2 concerns the separation of organic solvents (ethanol) from a protein solution using an inventive polymer.

The following classes of compounds may be mentioned as amines which are capable of reacting with at least two epoxide groups: primary aliphatic, cycloaliphatic, araliphatic or aromatic monoamines; aliphatic, cycloaliphatic, araliphatic or aromatic di- or polyamines with at least two primary or secondary amino groups; and furthermore aliphatic, cycloaliphatic, araliphatic or aromatic hydroxyamines with a primary amino group.

Examples which may be mentioned of representatives of these classes of compound are: primary aliphatic nonoamines: $C_1$–$C_{20}$-alkylamines, such as ethyl-, butyl-, i-pentyl-, n-hexyl-, 2-ethylhexyl-, dodecyl-, palmityl- and stearyl-amine. Primary cycloaliphatic monoamines: cyclohexylamine, cycloheptylamine and 2,4-dimethyl-cyclohexylamine; primary araliphatic amines: benzylamine and 2- and 4-methyl-benzylamine; primary aromatic amines: aniline, o-, m- and p-toluidines and xylidines; aliphatic di- and polyamines with at least two hydrogen atoms on (one) amino group(s): $C_2$–$C_6$-alkylenediamines, such as ethylene-, propylene-, butylene-, hexylene- and N,N-dimethyl-ethylene-diamine, poly-$C_2$–$C_4$-alkylene-polyamines, such as diethylenetriamine, dipropylenetriamine, bis-(3-aminopropyl)-methylamine, tris-(3-aminopropyl)-amine, triethylenetetramine and tripropylenetetramine; cycloaliphatic di- and polyamines with at least two hydrogen atoms on (one) amino group(s): 1,3- and 1,4-diaminocyclohexane, 1,2-bis-(4-aminocyclohexyl)-ethane, 1,2-bis-(4-aminocyclohexyl) ether, 1,2-bis-(4-aminocyclohexyl)-methylamine and 3,3-dimethyl-5-methyl-5-aminomethylcyclohexylamine; araliphatic di- and polyamines with at least hydrogen atoms on two (one) amino group(s): 1,3- and 1,4-bis(aminomethyl)-benzene; aromatic di- and polyamines with at least two hydrogen atoms on (one) amino group(s): p-phenylenediamine, 1,2-bis-(4-aminophenyl)-ethane, 1,2-bis(4-aminophenyl) ether, 1,2-bis-(4-aminophenyl)-methylamine and bis-(4-aminophenyl)-methane.

Aliphatic hydroxyamines with a primary amino group: 2-amino-1-ethanol, 3-amino-1-propanol, 4-amino-1-butanol and 2-amino-2-hydroxymethyl-propane-1,3-diol; cycloaliphatic hydroxyamines with a primary amino group: 4-amino-1-cyclohexanol and 2,2-dimethyl-4-amino-1-cyclohexanol; araliphatic hydroxyamines with a primary amino group: 4-amino-benzylamine.

$C_2$–$C_6$-Alkylenediamines and poly-$C_2$–$C_4$-alkylenepolyamines are preferably used.

The amines are employed in an amount such that only some, for example 5 to 90 mol %, preferably 15 to 45 mol %, of the epoxide groups contained in the polymerizable glycidyl compounds are reacted. That is to say, the amines are employed in an amount such that the content of epoxide groups in the crosslinked copolymers containing epoxide groups and basic amino groups is 1 to 27% by weight, preferably 5 to 20% by weight, based on the weight of the bead polymer.

To increase the mechanical stability and to produce the desired morphology of the bead polymers and/or to establish a certain degree of hydrophobicity, it may be advantageous for the polyglycidyl compounds to be cross-linked not only by reactions with the amines but additionally also with polyvinyl compounds which can be polymerized under free radical conditions. Possible polyvinyl compounds which can be polymerized under free radical conditions are, above all, aromatic divinyl compounds, such as divinylbenzene and divinyltoluene, aliphatic divinyl compounds, such as hexa-1,5-diene, hepta-1,6-diene, ethylene glycol dimethacrylate, methylene di(meth)acrylate and ethylene divinylurea, aromatic trivinyl compounds, such as trivinylbenzene, aliphatic trivinyl compounds, for example acrylic acid esters which are derived from polyhydric alcohols, such as glycerol, and triallyl cyanurate.

The polyvinyl compounds which can be polymerized under free radical conditions are employed in an amount of 0 to 35% by weight, based on the total weight of polymerizable monomers.

The agents which impart porosity which are known from the preparation of macroporous ion exchanger matrices are used as the agents which impart porosity. These are organic compounds which dissolve in the monomer but precipitate and, if appropriate, swell the polymer (precipitating agents or swelling agents for the polymer), for example aliphatic hydrocarbons, such as isododecane, octane, decane, dodecane and cyclohexane; alkyl-substituted aromatic hydrocarbons, such as toluene; $C_4$–$C_{14}$-alcohols, such as hexanol, cyclohexanol, octanol, decanol and methylisobutylcarbinol; aliphatic and aromatic chlorohydrocarbons, such as 1,1,1-trichloroethane, ethylene chloride, chlorobenzene and o-dichlorobenzene, or $C_1$–$C_{18}$-carboxylic acid esters, such as ethyl acetate, butyl acetate and amyl stearate.

The agents which impart porosity are employed in an amount of 50 to 200% by weight, preferably 90 to 150% by weight, based on the total weight of the monomers.

After preparation of the bead polymer, the agents which impart porosity are removed from this by evaporation or elution.

The bead-shaped, crosslinked, macroporous copolymers, containing epoxide groups and basic amino groups, according to the invention can be prepared in various ways, depending on whether the reaction of the polymerizable glycidyl compound with the amine is carried out before or during the bead polymerization.

According to procedure (a) (reaction of the polymerizable glycidyl compound with the amine before the bead polymerization), the polymerizable glycidyl compound and amine are initially reacted at temperatures from 0° to 100° C., preferably 20° to 70° C., if appropriate in the presence of the agent which imparts porosity or another diluent. The aqueous polymerization liquor and the mixture of polyvinyl compound, agent which forms free radical and—if the reaction of the glycidyl compound with the amine has been carried out in the absence of the agent which imparts porosity—the agent which imparts porosity are then added to the solution of the reaction product. If no polyvinyl compound is used, the agent which forms free radicals and which is required for the polymerization is dissolved either in the agent which imparts porosity or in a portion of the polymerizable glycidyl compound. The resulting aqueous suspensions are warmed to 50 to 100° C. to initiate the polymerization reaction and are kept at the chosen polymerization temperature until the polymerization has ended. After cooling, the bead polymer formed is separated off mechanically, for example by filtration, and is washed first with methanol and then with water and, if appropriate, dried.

Procedure (b) (reaction of the polymerizable glycidyl compound with the amine during the bead polymerization):

This is particularly easy to carry out; in this procedure, the monomers to be polymerized, the amine, the agent which imparts porosity and the agent which forms free radicals are added to the aqueous liquor at room temperature. The aqueous suspension is then warmed to 50° to 100° C., as described under procedure (a), in order to initiate the polymerization and is then stirred at the chosen polymerization temperature until the polymerization has ended. Working up of the resulting bead polymer is carried out as described under (a).

The bead polymers can be stored in solvent-moist or water-moist form.

In spite of the sensitivity of the epoxide groups to water, the content of epoxide groups in the resins falls by only 20% even on storage for 6 months.

The bead-shaped, crosslinked, macroporous copolymers, containing epoxide groups and basic amino groups, according to the invention are outstandingly suitable for binding biologically active substances, such as activators, inhibitors, antigens, antibodies, vitamins, antibiotics, proteins, living or dead cells and, in particular, enzymes, for example proteases, such as chymotrypsin or papain, invertases, esterases, ligases, glucose isomerase, lactase, glucose 6-phosphate dehydrogenase and the like.

By hydrolysis of the epoxide groups in the copolymers according to the invention, which can be achieved, for example, by treatment of the bead polymers with aqueous solutions which have a pH value of 1 to 3 at temperatures from 25° to 100° C., resins which contain hydroxyl groups and basic amino groups are obtained. These highly hydrophilic bead copolymers which contain hydroxyl groups and basic amino groups are suitable, for example, as chromatography resins for biomaterials.

The bead-shaped, crosslinked, macroporous copolymers, which contain epoxide groups and basic amino groups, according to the invention can furthermore be converted into strongly basic anion exchangers by reaction of the epoxide groups with amines and subsequent quaternization of the basic amino groups in the weakly basic anion exchangers thus obtained. These anion exchangers are distinguished not only by their excellent binding capacity for colloidal silicic acid, but also by their outstanding ease of regeneration.

The preparation of anion exchangers by reaction of copolymers which carry epoxide groups with amines is indeed known. Thus, the preparation of weakly basic anion exchangers by reaction of macroporous copolymers of glycidyl methacrylate and ethylene glycol di-methacrylate with amines is described in Angew. Makromol. Chemie 96 (1981) pages 69–84, and the preparation of strongly basic anion exchangers by reaction of macroporous copolymers of glycidyl methacrylate and ethylene glycol di-methacrylate with amines and subsequent quaternization with ethylene chlorohydrin is described in Angew. Makromol. Chemie 63 (1977) pages 23–36. However, neither the weakly basic nor the strongly basic anion exchangers are suitable for adsorption of colloidal silicic acid.

For binding of biologically active substances, it may be advantageous to provide the copolymers according to the invention with so-called spacers, and then to bind the biologically active substances in a known manner with the aid of glutaraldehyde.

EXAMPLE 1

190 g (1.34 mol) of glycidyl methacrylate and 10 g (0.17 mol) of ethylenediamine are stirred at 40° C. for 3 hours. A solution of 2 g of azodiisobutyronitrile in 200 g of butyl acetate and 1,000 ml of 0.2% strength by weight aqueous methylcellulose solution is then added to the mixture. The suspension is stirred at room temperature for a short time and then warmed to 70° C. and stirred at this temperature for 15 hours.

When the polymerization has ended, the bead polymer is filtered off with suction and eluted thoroughly in a chromatography column, first with methanol and then with water.

600 ml of bead polymer are obtained. The dried bead polymer has a content of
epoxide groups of 15.0% by weight
basic amino groups of 2.2% by weight

EXAMPLE 2

A mixture of 190 g (1.34 mol) of glycidyl methacrylate, 10 g (0.17 mol) of ethylenediamine, 200 g of a 1% strength solution of azodiisobutyronitrile in butyl acetate and 1,000 ml of 0.2% strength aqueous methylcellulose solution is stirred at room temperature for a short time. The suspension is then warmed to 70° C. and kept at this temperature for 15 hours. When the bead polymerization has ended and the bead polymer has been separated off, 450 ml of bead polymer are obtained.

The dried bead polymer has a content of
epoxide groups of 19.9% by weight=1.59 mol of epoxide groups of resin
basic amino groups: 1.1% by weight.

EXAMPLE 3

180 g (1.27 mol) of glycidyl methacrylate and 20 g (0.33 mol) of ethylenediamine are stirred at 40° C. for 3 hours. A solution of 2 g of azodiisobutyronitrile in 200 g of butyl acetate and 1,000 ml of 0.2% strength aqueous methylcellulose solution is then added to the mixture. The suspension is stirred at room temperature for a short time and then warmed to 70° C. and kept at this temperature for 15 hours.

The bead polymer is isolated as described in Example 1. 595 ml of bead polymer are obtained. The polymer has a content of
epoxide groups of 7.7% by weight
basic amino groups of 4.4% by weight

EXAMPLE 4

180 g (1.27 mol) of glycidyl methacrylate and 10 g (0.17 mol) of ethylenediamine are stirred at 40° C. for 3 hours. A solution of 2 g of azodiisobutyronitrile in 200 g of butyl acetate, 10 g (0.5 mol) of ethylene glycol dimethacrylate and 1,000 ml of 0.2% strength aqueous methylcellulose solution are then added to the mixture. The suspension is stirred at room temperature for a short time and then warmed to 70° C. and kept at this temperature for 15 hours. The bead polymer is then isolated as described in Example 1; 610 ml of bead polymer are obtained. The bead polymer has a content of
epoxide groups of 14.2% by weight
basic amino groups of 1.9% by weight

EXAMPLE 5

180 g (1.27 mol) of glycidyl methacrylate, 10 g (0.17 mol) of ethylenediamine, 10 g (0.07 mol) of divinylethyleneurea and a solution of 2 g of azodiisobutyronitrile are dispersed in 1,000 ml of 0.2% strength aqueous methylcellulose solution at room temperature. The suspension ss warmed to 70° C. and kept at this temperature for 15 hours.

The bead polymer is then isolated as described in Example 1; 520 ml of bead polymer are obtained. The bead polymer has a content of
epoxide groups of 18.5% by weight
basic amino groups of 1% by weight

EXAMPLE 6

A solution of 127 g (0.89 mol) of glycidyl methacrylate and 10 g (0.17 mol) of ethylenediamine in 300 g of methylisobutylcarbinol is stirred at 50° C. for 3 hours. 63 g (0.30 mol) of divinylbenzene (62% pure), 2 g of azodiisobutyronitrile and 1,500 ml of 0.2% strength aqueous methylcellulose solution is then added to the solution. The suspension is stirred at room temperature for a short time and thn warmed to 70° C. and kept at this temperature for 15 hours. The bead polymer is isolated as described in Example 1; 950 ml of bead polymer are obtained. The bead polymer has a content of
epoxide groups of 7.1% by weight
basic amino groups of 0.9% by weight

EXAMPLE 7

190 g (1.34 mol) of glycidyl methacrylate and 10 g (0.16 mol) of ethanolamine are stirred at 40° C. for 3 hours. A solution of 2 g of azodiisobutyronitrile in 200 g of butyl acetate and 1,000 ml of 0.2% strength aqueous methylcellulose solution is then added. The suspension is stirred at room temperature for a short time and then warmed to 70° C. and kept at this temperature for 15 hours. The bead polymer is isolated as described in Example 1. 840 ml of bead polymer are obtained. The bead polymer has a content of epoxide groups of 11.9% by weight
basic amino groups of 1.0% by weight

EXAMPLE 8

190 g (1.34 mol) of glycidyl methacrylate, 20 g (0.22 mol) of 50% strength aqueous ethylamine solution and a solution of 2 g of azodiisobutyronitrile in 200 g of butyl acetate are stirred together with 1,000 ml of 0.2% strength aqueous methylcellulose solution. The suspension is heated to 70° C. and kept at this temperature for 15 hours. The bead polymer is isolated as described in Example 1. 540 ml of bead polymer are obtained. The bead polymer has a content of epoxide groups of 13.9% by weight
basic amino groups of 0.6% by weight.

EXAMPLE 9

250 g of the bead polymer prepared and subsequently dried according to Example 1 are stirred with 1,500 g of 3-dimethylaminopropylamine at 40° C. for 20 hours. The resin is separated off from the excess amine by filtration with suction and then washed neutral, first with methanol and then with water. 1,220 ml of weakly basic anion exchanger (total capacity $T_C = 1.52$ equivalents of resin) are obtained.

400 ml of this weakly basic anion exchanger are stirred with 266 g of 45% strength NaOH, 800 ml of deioniozed water and 108.5 ml of methyl chloride in an autoclave at 40° C. for 16 hours. 1,100 ml of a strongly basic anion exchanger ($T_C$: 0.4 equivalent of resin) are obtained.

The average pore radius of the strongly basic anion exchanger is 2.0 $\mu$.

EXAMPLE 10

100 ml of the resin prepared according to Example 8 are stirred in dilute sulphuric acid at 100° C. for 20 hours and then washed neutral with completely demineralized water. The resin thus modified is then used for the following chromatographic separations:

(a) Desalination

Separation conditions:
Column:
  Length: 46.4 cm
  Internal diameter: 1.5 cm
  Particle diameter: 150–500 $\mu$
Application volume: 0.25 ml, 4% of albumin, 2% of NaCl
Elution: Phosphate buffer, pH 8
  Flow rate: 1.5 ml/minute.
The result of the separation is shown in FIG. 1.

(b) Removal of organic solvents

Separation conditions:
Column:
  Length: 46.4 cm
  Internal diameter: 1.5 cm
  Particle diameter: 150–200 $\mu$
Application volume: 0.25 ml, 4% of albumin, 2% of ethanol
Elution: Phosphate buffer, pH 8
  Flow rate: 1.5 ml/minute.
The result of the separation is shown in FIG. 2.

EXAMPLE 11

1 g of the resin prepared according to Example 3 is shaken with 50 ml of an esterase solution (633 units) in 0.1 molar phosphate buffer (pH 8.5) at room temperature for 36 hours. The resin is then filtered off with suction and washed thoroughly with buffer and water. The coupling yield of esterase is 31.2%.

If the resin described in Example 1 of European patent No. B1-0,058,767 is used instead of the resin employed, the coupling yield of esterase is only 17%.

What is claimed is:

1. A bead-shaped crosslinked macroporous copolymer which contains epoxide groups and basic amino groups and which is obtained by bead polymerizing a mixture comprising
   (a) a polymerizable vinyl glycidyl compound,
   (b) a porosity-imparting agent,
   (c) a free radical-forming agent, and
   (d) an amine capable of reacting with at least two epoxide groups and serving simultaneously as a crosslinking agent and as a basic modifier for the polymerizable glycidyl compounds, or comprising
   (b) and (c) as defined, and
   a pre-reaction product of (a) and (d) as defined,
   the amine being present in an amount such that the content of epoxide groups in the crosslinked copolymer is 1 to 27% by weight, the copolymer exhibiting a greater capacity for fixing enzymes without deactivation compared with a comparable copolymer wherein the same amine (d) is post-reacted.

2. The bead-shaped copolymer of claim 1, wherein the polymerizable glycidyl compound is a glycidyl (meth) acrylate or a glycidyl vinyl and/or a glycidyl allyl ether.

3. The bead-shaped copolymer of claim 1, wherein the amine which is capable of reacting with at least two epoxide groups is a primary aliphatic, cycloaliphatic, araliphatic or aromatic monoamine, an aliphatic cycloaliphatic, araliphatic or aromatic di- or polyamine with at least two hydrogen atoms on (one) amino group(s) or an aliphatic, cycloaliphatic, araliphatic or aromatic hydroxyamine with a primary amino group.

4. The bead-shaped copolymer of claim 1, wherein the amine is a $C_2$–$C_6$-alkylenediamine and/or a poly-$C_2C_4$-alkylenepolyamine.

5. The bead-shaped copolymer of claim 1, wherein the agent which imparts porosity is employed in an amount of 50 to 200% by weight, based on the total weight of the monomers.

6. A bead-shaped copolymer according to claim 1, wherein the agent which imparts porosity is selected from the group consisting of aliphatic hydrocarbons, alkyl-substituted aromatic hydrocarbons, $C_4$–$C_{14}$-alcohols, aliphatic chlorohydrocarbons, aromatic chlorohydrocarbons and $C_1$–$C_{18}$-carboxylic acid esters.

7. A bead-shaped copolymer according to claim 1, wherein the agent which imparts porosity is selected from the group consisting of isododecane, octane, decane, dodecane, cyclohexane, toluene, hexanol, cyclohexanol, octanol, decanol, methylisobutylcarbinol, 1,1,1-trichloroethane, ethylene chloride, chlorobenzene, o-dichlorobenzene, ethyl acetate, butylacetate and amylstearate.

8. A bead-chaped copolymer according to claim 1, wherein the agent which forms free radicals is azodiisobutyronitrile.

9. A copolymer according to claim 1, wherein the mixture subjected to bead polymerization further contains a polyvinyl compound which is polymerizable by free radical polymerization.

10. The bead-shaped copolymer of claim 9, wherein the polyvinyl compound which can be polymerized under free radical conditions is an aliphatic or an aromatic di- or trivinyl compound and/or triallyl cyanurate.

11. The bead-shaped copolymer of claim 9, wherein the polyvinyl compound which can be polymerized under free radical conditions is employed in an amount of 0 to 35% by weight, based on the total weight of polymerizable monomers.

12. A method for preparing a bead-shaped crosslinked macroporous copolymer which contains epoxide groups and basic amino groups, which comprises bead polymerizing a mixture comprising (a) a polymerizable vinyl glycidyl compound,
(b) a porosity-imparting agent,
(c) a free radical-forming agent, and
(d) a non-monomer amine capable of reacting with at least two epoxide groups and serving simultaneously as a crosslinking agent and as a basic modifier for the polyermizable glycidyl compounds or comprising (b) and (c) as defined, and a pre-reaction product of (a) and (d) as defined, the amine being present in an amount such that the content of epoxide groups in the crosslinked copolymer is 1 to 27% by weight, the copolymer exhibiting a greater capacity for fixing enzymes without deactivation compared with a comparable copolymer wherein the same amine (d) is post-reacted.

13. The method according to claim 12, wherein the mixture subjected to bead polymerization further contains a polyvinyl compound which is polymerizable by free radical polymerization.

* * * * *